United States Patent
Takano et al.

(10) Patent No.: US 11,298,107 B2
(45) Date of Patent: Apr. 12, 2022

(54) ULTRASONIC DIAGNOSTIC DEVICE AND ULTRASONIC PROBE

(71) Applicant: Hitachi, Ltd., Tokyo (JP)

(72) Inventors: Shinta Takano, Tokyo (JP); Kazuhiro Amino, Tokyo (JP); Hiroshi Kakita, Tokyo (JP)

(73) Assignee: FUJIFILM Healthcare Corporation, Kashiwa (JP)

(*) Notice: Subject to any disclaimer, the term of this patent is extended or adjusted under 35 U.S.C. 154(b) by 221 days.

(21) Appl. No.: 16/361,528

(22) Filed: Mar. 22, 2019

(65) Prior Publication Data
US 2020/0022677 A1   Jan. 23, 2020

(30) Foreign Application Priority Data

Jul. 19, 2018   (JP) .............................. JP2018-136159

(51) Int. Cl.
| | |
|---|---|
| *A61B 8/00* | (2006.01) |
| *A61B 8/08* | (2006.01) |
| *G01S 7/52* | (2006.01) |
| *G01S 15/89* | (2006.01) |

(Continued)

(52) U.S. Cl.
CPC .......... *A61B 8/4444* (2013.01); *A61B 8/4488* (2013.01); *A61B 8/5207* (2013.01); *A61B 8/5269* (2013.01); *A61B 8/56* (2013.01); *A61B 8/06* (2013.01); *A61B 8/13* (2013.01);
(Continued)

(58) Field of Classification Search
CPC ............... A61B 8/4444; G01S 15/8915; G01S 7/52019; G01S 7/5208
See application file for complete search history.

(56) References Cited

U.S. PATENT DOCUMENTS

| | | | |
|---|---|---|---|
| 2003/0018260 A1* | 1/2003 | Erikson ................. | B06B 1/0622 600/447 |
| 2005/0148874 A1* | 7/2005 | Brock-Fisher ...... | G01S 7/52049 600/447 |

(Continued)

FOREIGN PATENT DOCUMENTS

| | | |
|---|---|---|
| CN | 102612344 A | 7/2012 |
| CN | 105027219 A | 11/2015 |

(Continued)

OTHER PUBLICATIONS

Hassan, Basem Ahmed, "Low-Cost Digital Ultrasound Beamformer Design using Field Programmable Gate Arrays", Oct. 2012, Faculty of Engineering, Cairo University, p. 23, https://www.k-space.org/thesis/doc/Basem_Ahmed.pdf (Year: 2012).*

(Continued)

*Primary Examiner* — Katherine L Fernandez
*Assistant Examiner* — Taylor Deutsch
(74) *Attorney, Agent, or Firm* — Crowell & Moring LLP

(57) ABSTRACT

A plurality of transmission and reception circuits are connected to a plurality of vibration elements. The transmission and reception circuit includes a basic delay circuit and a fine delay circuit. The basic delay circuit delays a transmission signal and a reception signal for sub beamforming. The fine delay circuit is configured to be capable of performing delay finer than that of the basic delay circuit. A quantized delay error is compensated for by the fine delay circuit at the time of transmission.

7 Claims, 14 Drawing Sheets

(51) Int. Cl.
- *A61B 8/13* (2006.01)
- *A61B 8/06* (2006.01)

(52) U.S. Cl.
CPC ........... *A61B 8/488* (2013.01); *G01S 7/52033* (2013.01); *G01S 15/8915* (2013.01)

(56) References Cited

U.S. PATENT DOCUMENTS

| | | | |
|---|---|---|---|
| 2010/0228130 A1* | 9/2010 | Chiang | G10K 11/346 600/447 |
| 2011/0013488 A1 | 1/2011 | Ma et al. | |
| 2011/0181149 A1* | 7/2011 | Shikata | B06B 1/0629 310/327 |
| 2012/0113759 A1 | 5/2012 | Oshiki et al. | |
| 2013/0281863 A1 | 10/2013 | Chiang et al. | |
| 2016/0013782 A1 | 1/2016 | Nakagawa | |
| 2016/0287213 A1* | 10/2016 | Ishitsuka | A61B 8/5207 |
| 2016/0363657 A1 | 12/2016 | Nakagawa et al. | |
| 2018/0008234 A1 | 1/2018 | Kim et al. | |
| 2018/0192999 A1* | 7/2018 | Song | A61B 8/145 |
| 2018/0214123 A1 | 8/2018 | Takano | |
| 2018/0316225 A1* | 11/2018 | Yeo | H02M 7/2173 |

FOREIGN PATENT DOCUMENTS

| | | |
|---|---|---|
| JP | 2011-87948 A | 5/2011 |
| JP | 6205481 B2 | 9/2017 |
| WO | WO 2010/090160 A1 | 8/2010 |
| WO | WO 2017/026278 A1 | 2/2017 |
| WO | WO 2017/047329 A1 | 3/2017 |

OTHER PUBLICATIONS

Chinese-language Office Action issued in Chinese Application No. 201910223829.0 dated Oct. 26, 2021 with English translation (17 pages).

Japanese-language Office Action issued in Japanese Application No. 2018-136159 dated Feb. 15, 2022 with English translation (six (6) pages).

* cited by examiner

FIG. 9

Table 164:

| QUANTIZED DELAY ERROR IN UNITS OF ROW/ IN UNITS OF COLUMN | COMPENSATION DELAY TIME | CONTROL CODE (Ra/Rb) |
|---|---|---|
| -0.5 TO -0.25 | 0 | 00 |
| -0.25 TO 0.25 | 0.5 | 01 |
| 0.25 TO 0.5 | 1.0 | 11 |

168 / 170 / 172

Table 174:

| COLUMN CONTROL CODE Rb | ROW CONTROL CODE Ra | | |
|---|---|---|---|
| | 00 | 01 | 11 |
| 00 | 0 | 1 | 2 |
| 01 | 1 | 2 | 3 |
| 11 | 2 | 3 | 4 |

166

ULTRASONIC DIAGNOSTIC DEVICE AND ULTRASONIC PROBE

BACKGROUND OF THE INVENTION

1. Field of the Invention

The present invention relates to an ultrasonic diagnostic device and an ultrasonic probe, and more particularly, to sub beamforming technology for transmission.

2. Description of Related Art

In three-dimensional ultrasonic diagnostic, volume data is acquired from the inside of a living body through two-dimensional scanning of an ultrasonic beam, and a three-dimensional ultrasonic image, a two-dimensional ultrasonic image, and the like are formed on the basis of the volume data. In general, a three-dimensional ultrasonic image is an image three-dimensionally expressing a tissue in a living body, and a two-dimensional ultrasonic image is an image expressing a cross section of a tissue in a living body. A blood flow in a living body may be displayed as a three-dimensional ultrasonic image or a two-dimensional ultrasonic image.

In three-dimensional ultrasonic diagnostic, an ultrasonic probe (3D probe) including a two-dimensional vibration element array is usually used. A two-dimensional vibration element array is constituted by, for example, thousands, tens of thousands, or hundreds of thousands of vibration elements arrayed two-dimensionally. In order to supply a transmission signal to each vibration element and to process a signal received from each vibration element, an electronic circuit for sub beamforming for channel reduction is provided within an ultrasonic probe.

International Publication No. WO 2017/026278 discloses an element circuit array provided within an ultrasonic probe. Row unit delay control and column unit delay control are applied to the element circuit array. International Publication No. WO 2017/047329 discloses a technique for performing sub beamforming within an ultrasonic probe in a stepwise manner. Japanese Patent No. 6205481 discloses a plurality of analog delay circuits provided within an ultrasonic probe. Each of the analog delay circuits is constituted by a plurality of delay cells (capacitors).

In a case where transmission sub beamforming is performed within an ultrasonic probe, it is necessary to provide an electronic circuit including a plurality of delay circuits within the ultrasonic probe. When an operation speed of the electronic circuit increased, the accuracy of delay can be improved, but a circuit scale is increased due to the necessity of securing a certain amount of delay, which results in an increase the amount of control accordingly. Accordingly, it is not possible to easily increase an operation speed of the electronic circuit. However, when an operation speed of the electronic circuit is controlled, a sufficient accuracy of delay is not obtained for individual transmission signals.

SUMMARY OF THE INVENTION

An object of the present invention is to achieve both the suppression of an increase in a circuit scale and an improvement in the accuracy of transmission delay in an ultrasonic probe. Alternatively, an object of the present invention is to be able to compensate for a delay error for each vibration element in an ultrasonic probe.

An ultrasonic diagnostic device according to the present invention includes a vibration element array which is provided within an ultrasonic probe and is constituted by a plurality of vibration elements arrayed two-dimensionally, and an element circuit array which is provided within the ultrasonic probe, is constituted by a plurality of element circuits connected to the plurality of vibration elements, and has a sub beamforming function, in which each of the element circuits includes a basic delay circuit which delays a transmission signal, and a fine delay circuit which is configured to be capable of performing delay finer than that of the basic delay circuit and delays a transmission signal output from the basic delay circuit.

An ultrasonic probe according to the present invention includes a vibration element array which is constituted by a plurality of vibration elements and an element circuit array which is constituted by a plurality of element circuits connected to the plurality of vibration elements, in which each of the element circuits includes a basic delay circuit which delays a transmission signal, and a fine delay circuit which is configured to be capable of performing delay finer than that of the basic delay circuit and delays a transmission signal output from the basic delay circuit.

According to the present invention, it is possible to achieve both the suppression of an increase in a circuit scale and an improvement in the accuracy of transmission delay in an ultrasonic probe. Alternatively, according to the present invention, it is possible to compensate for a delay error for each vibration element in an ultrasonic probe.

BRIEF DESCRIPTION OF THE DRAWINGS

FIG. 9 is a diagram illustrating compensation control according to the first example;

DESCRIPTION OF EMBODIMENTS

Figure 1:
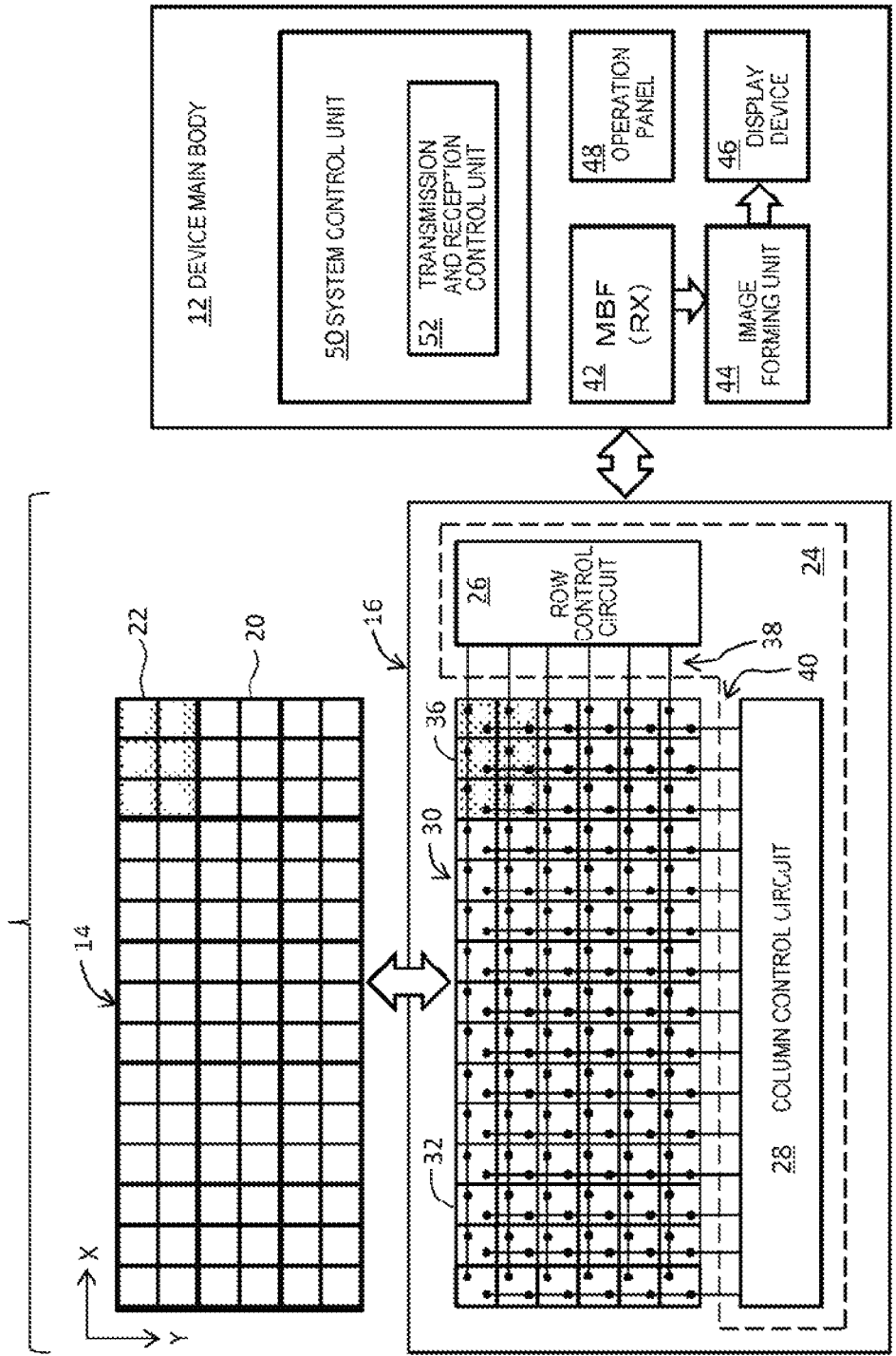
FIG. 1 is a block diagram illustrating a configuration of an ultrasonic diagnostic device according to an embodiment.

Hereinafter, an embodiment will be described with reference to the accompanying drawings.

(1) Outline of Embodiment

An ultrasonic diagnostic device according to the embodiment includes an ultrasonic probe. The ultrasonic probe includes a vibration element array and an element circuit array. The vibration element array is constituted by a plurality of vibration elements arrayed two-dimensionally. The element circuit array is constituted by a plurality of element circuits connected to the plurality of vibration elements and has a sub beamforming function. Each of the element circuits includes a basic delay circuit delaying a transmission signal, and a fine delay circuit configured to be capable of performing delay finer than that of the basic delay circuit and delaying a transmission signal output from the basic delay circuit.

According to the above-described configuration, delay (fine delay) performed by the fine delay circuit can be applied to a transmission signal subjected to delay (basic delay) performed by the basic delay circuit in the element circuits. Further, in the element circuits, it is possible to locally restrict a portion where the quantity of materials increases to improve the accuracy of delay. Therefore, according to the above-described configuration, it is possible to achieve both an improvement in the accuracy of delay and the suppression of an increase in a circuit scale. The element circuits are equivalent to transmission and reception circuits to be described later. The fact that the fine delay circuit can perform delay finer than that of the basic delay circuit means that a unit delay time (minimum delay time) of the fine delay circuit is shorter than a unit delay time of the basic delay circuit. It can also be understood that the fine delay circuit operates at a higher speed than that of the basic delay circuit as a whole.

In the embodiment, the basic delay circuit operates according to a basic clock, and the fine delay circuit operates according to a plurality of clocks having different phases with one another generated from the basic clock or according to a clock which is generated from the basic clock at a higher speed than that the basic clock. For example, a plurality of clocks having different phases and having the same frequency as that of the basic clock may be generated on the basis of the basic clock, and the plurality of clocks may be given to the fine delay circuit. Alternatively, a high-speed clock having a higher frequency than that of the basic clock may be generated on the basis of the basic clock, and the high-speed clock may be given to the fine delay circuit. As such a high-speed clock, a plurality of high-speed clocks having different phases may be generated, and the high-speed clocks may be given to the fine delay circuit. Clocks required for fine delay may be individually generated within individual element circuits, or a clock required for fine delay may be generated by a circuit other than the element circuit array and then used in common in the plurality of element circuits. In the embodiment, the unit delay time of the fine delay circuit is l/n times the unit delay time of the basic delay circuit. For example, n is an integer equal to or greater than 2.

In the embodiment, the fine delay circuit includes a delay device column to which a transmission signal output from the basic delay circuit is input and which is constituted by a plurality of delay devices connected to each other in series, and a selection device that selects anyone candidate signal from among a plurality of candidate signals output from the delay device column delayed in a stepwise manner as a transmission signal subjected to fine delay in accordance with a control signal. In this configuration, a signal to be actually used is selected from among a plurality of candidate signals general in parallel. According to the above-described configuration, it is possible to realize the fine delay circuit with a relatively simple configuration.

The ultrasonic diagnostic device according to the embodiment includes a control circuit that applies matrix control which is a combination of row unit delay control and column unit delay control to the element circuit array, a row control signal for compensating for a delay error occurring through the row unit delay control and a column control signal for compensating for a delay error occurring through the column unit delay control are given to each of the element circuits, and the fine delay circuits delay a transmission signal in accordance with the row control signal and the column control signal.

According to the matrix control, it is possible to drastically reduce the number of signal lines and the amount of control, as compared with a case where the signal lines are individually connected to the individual vibration elements and pieces of delay data are individually given to the individual vibration elements. On the other hand, according to such matrix control, a delay error (for example, a quantized error) through row unit delay control and a delay error (for example, a quantized error) through column unit delay control occur. In the above-described configuration, such two delay errors are collectively compensated for each vibration element.

In the embodiment, a first control signal and a second control signal for compensating for a delay error are given to each of the element circuits, a delay amount of the basic delay circuit is corrected on the basis of the first control signal, and a delay amount of the fine delay circuit is selected on the basis of the second control signal. In this configuration, a delay error is compensated for by a combination of two compensation methods. For example, an integer portion of a compensation delay amount may be compensated for in the basic delay circuit, and a decimal portion of a correction delay amount may be compensated for in the fine delay circuit. In this case, a portion of the integer portion may be compensated for in the basic delay circuit. Although the circuit scale of the fine delay circuit is increased in a case where the fine delay circuit performs compensation of the entire integer portion, it is possible to reduce the circuit scale of the fine delay circuit according to the above-described configuration. For example, when tens of thousands of element circuits are provided corresponding to tens of thousands of vibration elements, a reduction in a portion of the configuration of each of the element circuits leads to a reduction effect which is tens of thousands times as much as the whole element circuit array.

The ultrasonic diagnostic device according to the embodiment includes a control circuit that applies matrix control which is a combination of row unit delay control and column unit delay control to the element circuit array, a first row control signal for compensating for a delay error occurring through row unit delay control and a first column control signal for compensating for a delay error occurring column unit delay control are given to each of the element circuits as the first control signal, a second row control signal for compensating for a delay error occurring through row unit delay control and a second column control signal for compensating for a delay error occurring through column unit delay control are given to each of the element circuits as the second control signal, a basic delay controller that corrects a delay amount of the basic delay circuit in accordance with the first row control signal and the first column control signal is provided, and a fine delay controller that selects a delay amount of the fine delay circuit in accordance with the second row control signal and the second column control signal is provided.

In the above-described configuration, a delay error in units of a row and a delay error in units of a column which occur in matrix control are collectively compensated for by a combination of two compensation methods.

The ultrasonic diagnostic device according to the embodiment includes a transmission main beamformer and a transmission sub beamformer group provided between the transmission main beamformer and the vibration element array, and the transmission sub beamformer group is constituted by the element circuit array. Alternatively, the ultrasonic diagnostic device according to the embodiment includes a transmission main beamformer and a plurality of transmission sub beamformers groups provided between the transmission main beamformer and the vibration element array in a stepwise manner, and a transmission sub beamformer group closest to the vibration element array among the plurality of transmission sub beamformers groups is constituted by the element circuit array. As described above, a basic delay circuit and a fine delay circuit are provided within each element circuit, the basic delay circuit is a delay circuit for transmission sub beamforming, and the fine delay circuit is a circuit for compensating for a transmission delay error. In the embodiment, one or a plurality of transmission sub beamformers groups are provided within the ultrasonic probe. The transmission main beamformer is provided within the ultrasonic probe or within the main body of the ultrasonic diagnostic device. Even when delay errors accumulate in stepwise sub beamforming and delay errors accumulate through row unit control and column unit control, it is possible to collectively compensate for the accumulated delay errors for each vibration element according to the above-described configuration.

In the embodiment, the basic delay circuit is a delay circuit for transmission and reception, and the fine delay circuit is a delay circuit for transmission. It is also possible to make the fine delay circuit function at the time of reception. However, since reception dynamic focus is generally applied at the time of reception, the configuration and control of the fine delay circuit become considerably complicated in order to cope with the reception dynamic focus. Accordingly, in the embodiment, the fine delay circuit is made to function at the time of transmission.

The ultrasonic probe according to the embodiment includes a vibration element array constituted by a plurality of vibration elements and an element circuit array constituted by a plurality of element circuits connected to the plurality of vibration elements. Each of the element circuits includes a basic delay circuit delaying a transmission signal and a fine delay circuit configured to be capable of performing delay finer than that of the basic delay circuit and delaying a transmission signal output from the basic delay circuit.

In the above-described configuration, fine delay is executed for each vibration element within the ultrasonic probe, and thus an improvement in the accuracy of delay is achieved while suppressing an increase in a circuit scale. Although a two-dimensional vibration element array is provided as the vibration element array in the embodiment, a one-dimensional vibration element array may be provided.

(2) Details of Embodiment

In FIG. 1, a configuration of the ultrasonic diagnostic device according to the embodiment is illustrated as a block diagram. The ultrasonic diagnostic device is a medical device which is provided in a medical institution such as a hospital and forms an ultrasonic image on the basis of a reception signal obtained by transmitted and received ultrasonic waves with respect to a living body (examinee). The ultrasonic diagnostic device according to the embodiment has a function of forming a three-dimensional ultrasonic image and the like on the basis of volume data acquired from a three-dimensional space in a living body. Tissues to be diagnosed are, for example, a liver, a heart, a fetus, and the like. The ultrasonic diagnostic device is constituted by an ultrasonic probe 10 and a device main body 12.

The ultrasonic probe 10 is a 3D probe. That is, the ultrasonic probe forms a three-dimensional echo data fetching space within a living body through electronic two-dimensional scanning of an ultrasonic beam. Volume data is acquired from the three-dimensional echo data fetching space. The ultrasonic probe 10 includes a vibration element array 14 and an electronic circuit 16. Actually, the ultrasonic probe 10 includes a probe head, a cable, and a connector, and the vibration element array 14 and the electronic circuit 16 are disposed within the probe head. A wave transmitting/receiving surface (acoustic lens surface) of the ultrasonic probe 10 abuts on the surface of a living body, and ultrasonic waves are transmitted and received in this state. A body cavity insertion type probe may be used instead of a body surface abutting type probe.

The vibration element array 14 is constituted by a plurality of vibration elements 20 arrayed two-dimensionally. In FIG. 1, an X-direction is a first element array direction, and a Y-direction is a second element array direction. The plurality of vibration elements 20 may be arrayed on a plane or may be arrayed on a curved surface. The vibration element array 14 is constituted by, for example, thousands, tens of thousands, or hundreds of thousands of vibration elements 20. In the vibration element array 14, a plurality of sub-arrays 22 are set. Transmission main beamforming (and reception main beamforming) is executed with the sub-arrays 22 as processing units (delay processing units), and transmission sub beamforming (and reception sub beamforming) is executed with the vibration elements 20 as processing units within the individual sub-arrays 22. As will be described later, the sub-arrays 22 may further be partitioned into a plurality of sections. In this case, transmission sub beamforming (and reception sub beamforming) of a first stage is executed with sections as processing units in the sub-arrays 22, and transmission sub beamforming (and reception sub beamforming) of a second stage is executed with the vibration elements 20 within the sections. Meanwhile, as will be described later, a transmission main beamformer may be provided within the ultrasonic probe 10 or within the device main body 12. A reception main beamformer is usually provided within the device main body 12.

In the embodiment, the electronic circuit 16 is constituted by one or a plurality of semiconductor integrated circuits. The electronic circuit 16 has a digital signal processing function and an analog signal processing function. Specifically, as illustrated in the drawing, the electronic circuit 16 includes a transmission and reception circuit array (element circuit array) 30 and a control circuit 24. The transmission and reception circuit array 30 is constituted by a plurality of transmission and reception circuits (an element circuit and a transmission and reception cell) 32 which are connected to the plurality of vibration elements 20. The plurality of transmission and reception circuits 32 are connected to the plurality of vibration elements 20 on a one-to-one basis. In the embodiment, each of the transmission and reception circuits 32 includes a basic delay circuit functioning at the time of transmission and reception and a fine delay circuit functioning at the time of transmission. These circuits will be described later in detail. A function as a transmission main beamformer may be exhibited in each of the transmission and reception circuits 32.

The transmission and reception circuit array 30 is constituted by a plurality of groups 36 corresponding to the plurality of sub-arrays 22. The plurality of transmission and reception circuits 32 constituting each of the groups 36 function as sub beamformers. As described above and will be described later in detail, in a case where a plurality of sub beamformer groups are provided hierarchically, the transmission and reception circuit array 30 illustrated in the drawing is equivalent to a sub beamformer group closet to the vibration element array 14 among the plurality of sub beamformer groups.

The control circuit 24 is a circuit that controls operations of circuits included in the electronic circuit 16. In the embodiment, the control circuit 24 includes a row control circuit (row unit delay control circuit) 26 and a column control circuit (column unit delay control circuit) 26 for executing matrix control (row/column control). When pieces of delay data for sub beamforming are individually given to the transmission and reception circuit array 30 in units of a transmission and reception circuit, the amount of control increases significantly. On the other hand, in the embodiment, a row control signal (row unit delay control signal) is given to the transmission and reception circuit array 30 in units of a row, and a column control signal (column unit delay control signal) is given thereto in units of a column. A specific row control signal and a specific column control signal are input to each of the transmission and reception circuits 32. These signals indicate a representative delay time in units of a row and a representative delay time in units of a column. In each of the transmission and reception circuits 32, a delay time (a basic delay time for sub beamforming) is determined by addition of two representative delay times or a method equivalent thereto, and thus the basic delay circuit operates. It is also possible to obtain a fixed accuracy of delay through such matrix control. Meanwhile, in general, a delay time for sub beamforming is considerably shorter than a delay time for main beamforming, which can be referred to as a minute delay time. However, the delay time for sub beamforming should be distinguished from a fine delay time for delay compensation. In the embodiment, a unit delay time (minimum delay time) in the basic delay circuit is twice a unit delay time in the fine delay circuit. Conversely, the latter unit delay time is half of the former unit delay time.

Specifically, a representative delay time in units of a row and a representative delay time in units of a column are an average delay time in units of a row and an average delay time in units of a column, respectively. An upper limit value may be provided for each of the average delay time in units of a row and the average delay time in units of a column. A weighting addition value, an average value, and the like may be used instead of the above-described addition value. The average delay time in units of a row and the average delay time in units of a column may be made to function as delay control parameters independent of each other without being added.

According to matrix control, a quantized delay error (an error on a time axis resulting from the frequency of the basic clock) occurs in both row and column directions. Furthermore, in a case where stepwise sub beamforming of two or more stages is applied, quantized delay errors occurring in the respective stages are also accumulated. It is desirable to compensate for such quantized delay error. For this reason, in the embodiment, a fine delay circuit for compensating for a quantized delay error (and other delay errors) in units of a vibration element is provided within each of the transmission and reception circuits 32.

As illustrated in the drawing, a plurality of row control signals are output from the row control circuit 26, and specifically, the row control circuit 26 is connected to the transmission and reception circuit array 30 through a plurality of row signal lines 38. One row is constituted by the plurality of transmission and reception circuits 32 lined up in a row direction, and a common row signal line is connected thereto in parallel. On the other hand, a plurality of column control signals are output from a column control circuit 28, and specifically, the column control circuit 28 is connected to the transmission and reception circuit array 30 through a plurality of column signal lines 40. One column is constituted by the plurality of transmission and reception circuits 32 lined up in a column direction, and a common column signal line is connected thereto in parallel.

Subsequently, the device main body 12 will be described. In FIG. 1, a main configuration of the device main body 12 is illustrated. A reception main beamformer 42 is a reception circuit and executes reception main beamforming. That is, phasing addition (delay addition) is applied to a plurality of reception signals (reception signals after sub beamforming) to be input. Thereby, beam data is generated for each ultrasonic beam. For example, one piece of volume data is constituted by a plurality of pieces of frame data, one piece of frame data is constituted by a plurality of pieces of beam data, and one piece of beam data is constituted by a plurality of pieces of echo data.

An image forming unit 44 forms a three-dimensional ultrasonic image on the basis of volume data. A two-dimensional ultrasonic image may be formed. A three-dimensional or two-dimensional blood flow image may be formed. The image forming unit 44 is constituted by one or a plurality of processors. The image forming unit 44 may be configured as a function of a program executed in a CPU. An ultrasonic image is displayed on a display device 46. The display device 46 is constituted by an LCD, an organic EL display panel, or the like. An operation panel 48 functions as an input device and includes a plurality of switches, a plurality of buttons, a trackball, a keyboard, and the like.

A system control unit 50 controls operations of components within the ultrasonic diagnostic device. The system control unit 50 is constituted by a CPU and a program. The system control unit 50 has a transmission and reception control function which is expressed as a transmission and reception control unit 52. The transmission and reception control unit 52 controls the reception main beamformer 42 and the like within the device main body 12 and controls the electronic circuit 16 within the ultrasonic probe 10. Individual row average delay times and individual column average delay times are calculated by the transmission and reception control unit 52 at the time of transmission and reception, and data indicating results of the calculation is transmitted from the transmission and reception control unit 52 to the control circuit within the electronic circuit 16. In addition, a row compensation delay time and a column compensation delay time required in a case where fine delay is performed for each vibration element are calculated by the transmission and reception control unit 52 at the time of transmission, and data indicating results of the calculation is transmitted from the transmission and reception control unit 52 to the control circuit 24 within the electronic circuit 16.

Figure 2:
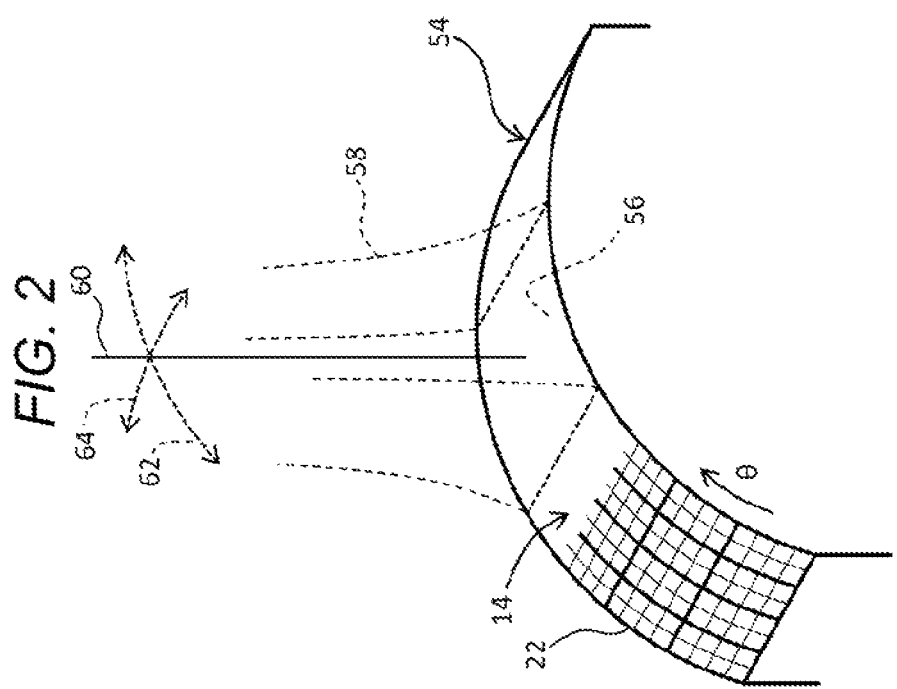
FIG. 2 is a perspective view illustrating an example of an ultrasonic probe.

In FIG. 2, a convex type ultrasonic probe 54 is schematically illustrated. The ultrasonic probe 54 includes the vibration element array 14 illustrated in FIG. 1. The vibration element array 14 is curved along a cylindrical surface or a convex surface. The plurality of sub-arrays 22 are set for the vibration element array 14. A portion of the vibration element array 14 constitutes a transmission opening 56, and a transmission beam 58 is formed using the transmission opening 56. Reference numeral 60 denotes a central axis of the transmission beam 58. For example, when electronic linear scanning is performed on the transmission opening in a e-direction, the transmission beam 58 moves in the e-direction (see reference numeral 62). When electronic sector scanning is applied in a direction perpendicular to the e-direction while fixing the transmission opening 56, the transmission beam 58 moves in a direction perpendicular to the e-direction (see reference numeral 64). Electronic sector scanning may be applied in the e-direction. Various electronic scanning methods may be applied at the time of two-dimensional scanning of an ultrasonic beam. The ultrasonic probe 54 illustrated in the drawing is an example, and other ultrasonic probes can be used.

Hereinafter, a configuration and control related to transmission will be described in detail.

Figure 3:
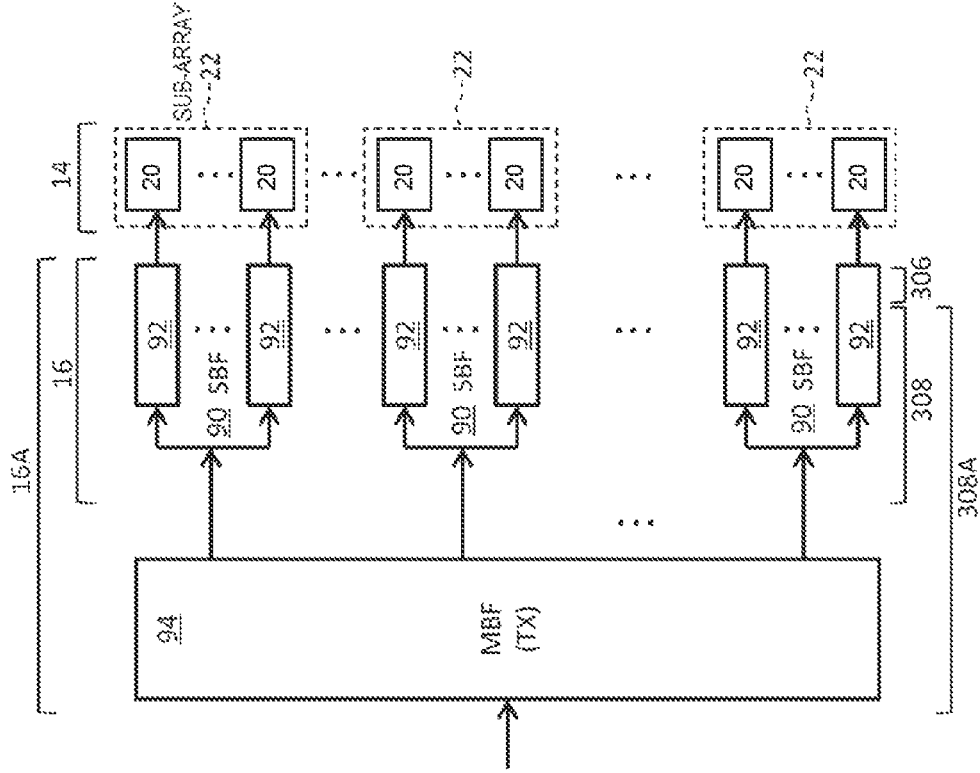
FIG. 3 is a block diagram illustrating a first configuration example for transmission beamforming.

In FIG. 3, a first configuration example is illustrated. The vibration element array 14 is constituted by a plurality of vibration elements. The plurality of sub-arrays 22 are set for the vibration element array 14. A plurality of transmission sub beamformers (transmission SBFs) 90 are provided in parallel between a transmission main beamformer (transmission MBF) 94 and the vibration element array 14. The transmission SBF 90 is constituted by a plurality of delay circuits 92 (for convenience of description, the plurality of delay circuits 92 corresponding to one sub-array 22 are referred to as the transmission SBF 90). The delay circuits 92 are connected to a plurality of vibration elements within the sub-array 22 on a one-to-one basis. In the transmission MBF 94, a plurality of transmission signals having been subjected to delay processing are generated and the signals are supplied to the plurality of transmission SBFs 90. In the transmission SBFs 90, delay processing is applied to the input transmission signal to generate a plurality of transmission signals to be supplied to a plurality of vibration elements constituting each sub-array. The individual delay circuits 92 are equivalent to the above-described transmission and reception circuits (see reference numeral 32 in FIG. 1). In other words, a transmission and reception circuit array functions as the plurality of transmission SBFs 90. The plurality of transmission SBFs 90 are provided within the electronic circuit 16. As indicated by reference numeral 16A, the transmission MBF 94 may be provided within the electronic circuit in addition to the plurality of transmission SBFs 90.

Circuits within the electronic circuit 16 basically operate in synchronization with the basic clock having a basic frequency. However, a fine delay circuit provided at a final stage of each of the transmission and reception circuits within the electronic circuit 16 operates at a high speed in synchronization with a pair of clocks for fine delay generated from the basic clock, as will be described later. A portion operating at a specified speed in accordance with the basic clock within the electronic circuit 16 is denoted by reference numeral 308, and a portion operating at a higher speed than a specified speed within the electronic circuit 16 (a portion capable of performing delay finer than that of the basic delay circuit) is denoted by reference numeral 306. When a portion operating at a high speed or a portion having a complicated configuration is locally limited within the electronic circuit 16, it is possible to reduce a problem of an increase in a circuit scale and the complication of control. On the other hand, it is possible to obtain the accuracy of delay which has not been realized so far by delay error compensation. In a case where the transmission MBF 94 is provided within the electronic circuit 16, a portion denoted by reference numeral 308A is a portion operating at a specified speed.

Figure 4:
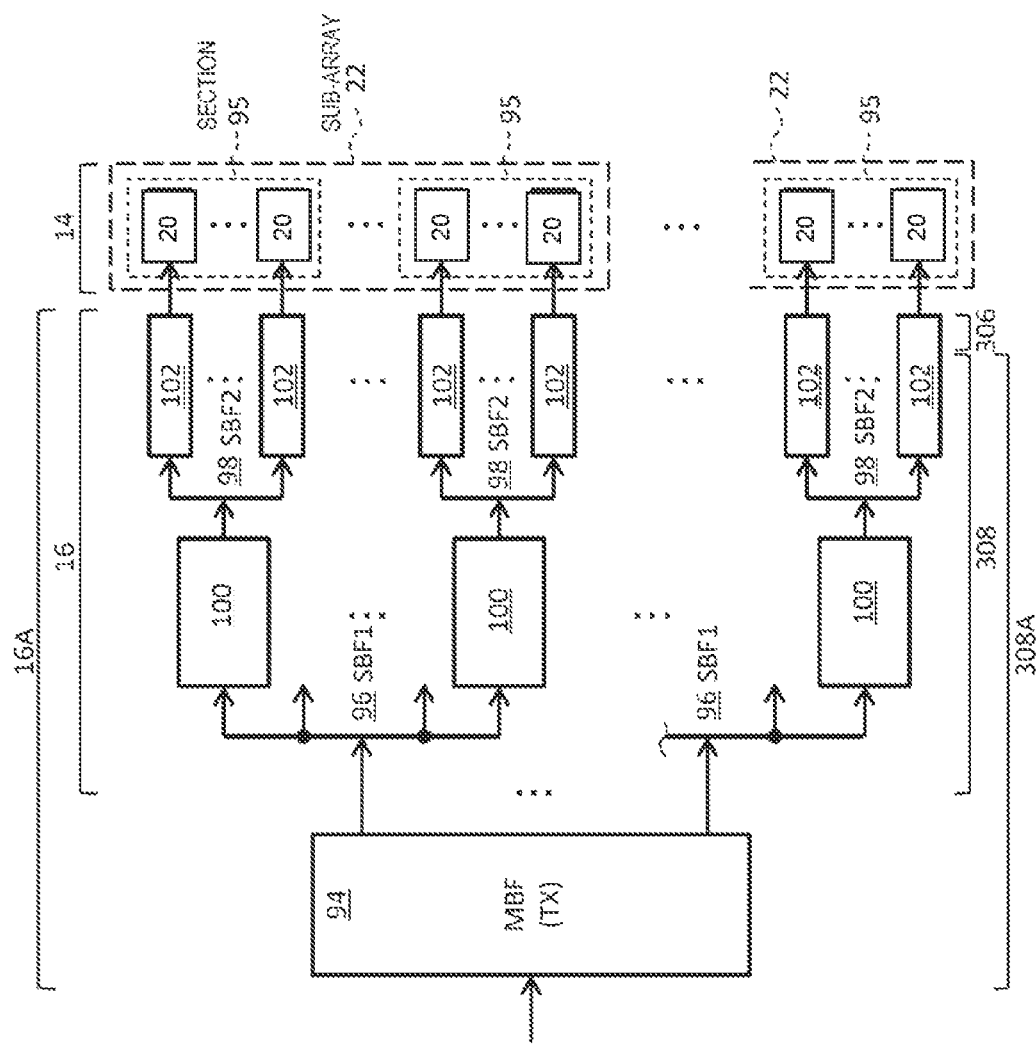
FIG. 4 is a block diagram illustrating a second configuration example for transmission beamforming.

In FIG. 4, a second configuration example is illustrated. The same components as those illustrated in FIG. 3 are denoted by the same reference numerals, and the description thereof will be omitted.

The plurality of sub-arrays 22 are set in the vibration element array 14, and each of the sub-arrays 22 is partitioned into a plurality of sections 95. Transmission sub beamforming of a first stage is executed with sections within each of the sub-arrays 22 as processing units, and transmission sub beamforming of a second stage is executed with vibration elements within each of the sections 95 as processing units. Specifically, two transmission sub beamformer groups are provided between the transmission MBF 94 and the vibration element array 14. A first transmission sub beamformer group is constituted by a plurality of transmission SBF1s (96), and a second transmission sub beamformer group is constituted by a plurality of transmission SBF2s (98). Each of the transmission SBF1s (96) is constituted by a plurality of delay circuits 100, and each of the transmission SBF2s (98) is constituted by a plurality of delay circuits 102. Each of the delay circuits 102 is equivalent to the above-described transmission and reception circuit (see reference numeral 32 in FIG. 1). In general, a k-stage transmission SBF group can be provided between the transmission MBF 94 and the vibration element array 14. Here, k is an integer equal to or greater than 1. In either case, it is preferable to provide a fine delay circuit at a location closest to the vibration element array 14 in units of a vibration element.

A quantized delay error and the compensation therefor will be described on the basis of FIG. 5. The transmission opening 56 set in a vibration element array is illustrated in the upper portion of FIG. 5. Although the transmission opening 56 has a rectangular shape, the shape may be an elliptical shape or other shapes. Here, a specific row 70 and a specific column 72 within the transmission opening 56 are brought into focus. A vibration element 74 is present at an intersection point between the row 70 and the column 72.

Figure 5:
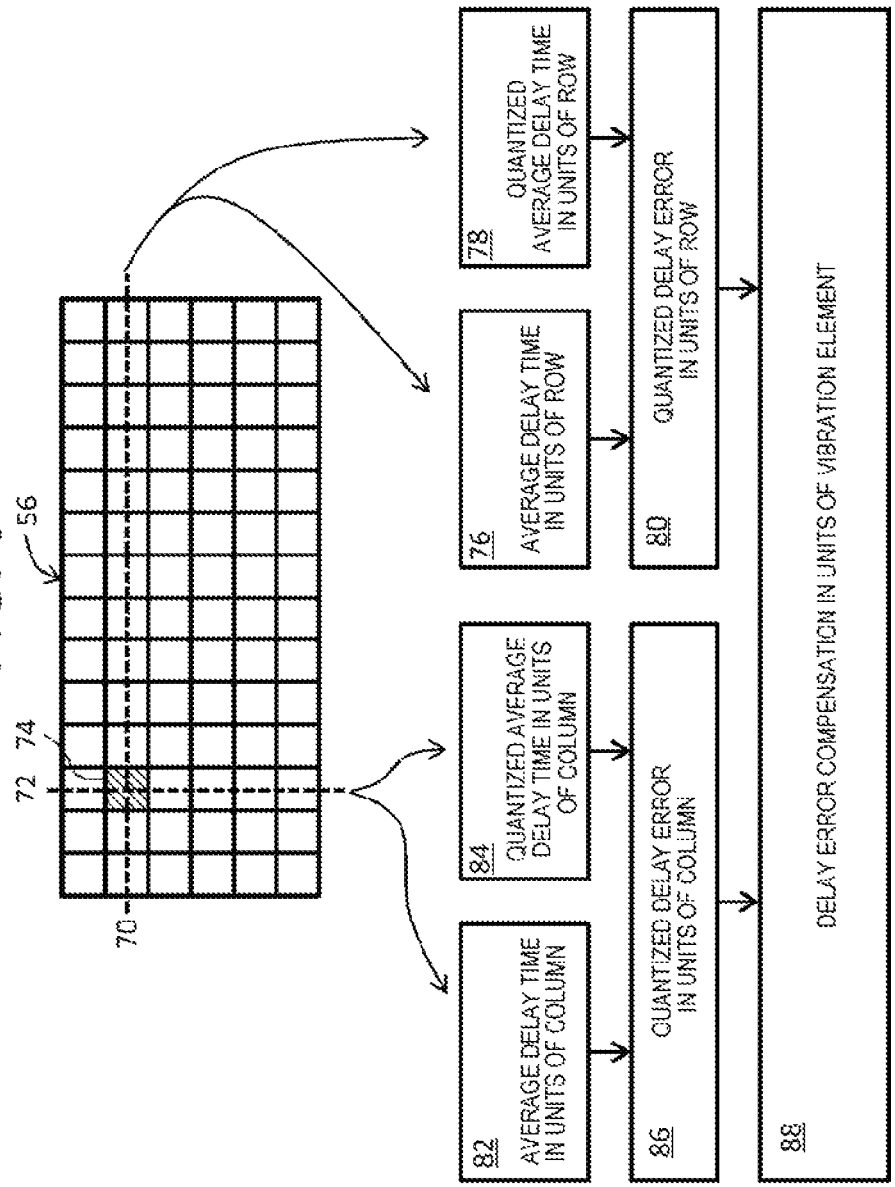
FIG. 5 is a diagram illustrating a delay error and delay error compensation.

As illustrated in the lower portion of FIG. 5, an average delay time 76 in units of a row is an ideal average delay time (not having a quantized error) which is given to the row 70. On the other hand, actually, an average delay time 78 in units of a row which includes a quantized delay error (quantized average delay time in units of a row) is given to the row 70. For example, a quantized error is a maximum of 25 ns in a case where the frequency of the basic clock is 40 MHz, and a quantized error is a maximum of 20 ns in a case where the frequency of the basic clock is 50 MHz. A difference between the average delay time 76 in units of a row and the quantized average delay time 78 in units of a row is a quantized delay error 80 in units of a row.

Similarly, an average delay time 82 in units of a column is an ideal average delay time (not having a quantized error) which is given to the column 72. On the other hand, actually, an average delay time 84 in units of a column which includes a quantized delay error (quantized average delay time in units of a column) is given to the column 72. A difference between the average delay time in units of a row 82 and the quantized average delay time 84 in units of a column is a quantized delay error 86 in units of a column.

In matrix control, a quantized delay error caused by adding up two quantized delay errors 80 and 86 occurs for each vibration element. Consequently, as denoted by reference numeral 88, a quantized delay error is compensated for in units of a vibration element. This compensation is performed by a fine delay circuit provided for each vibration element.

Figure 6:
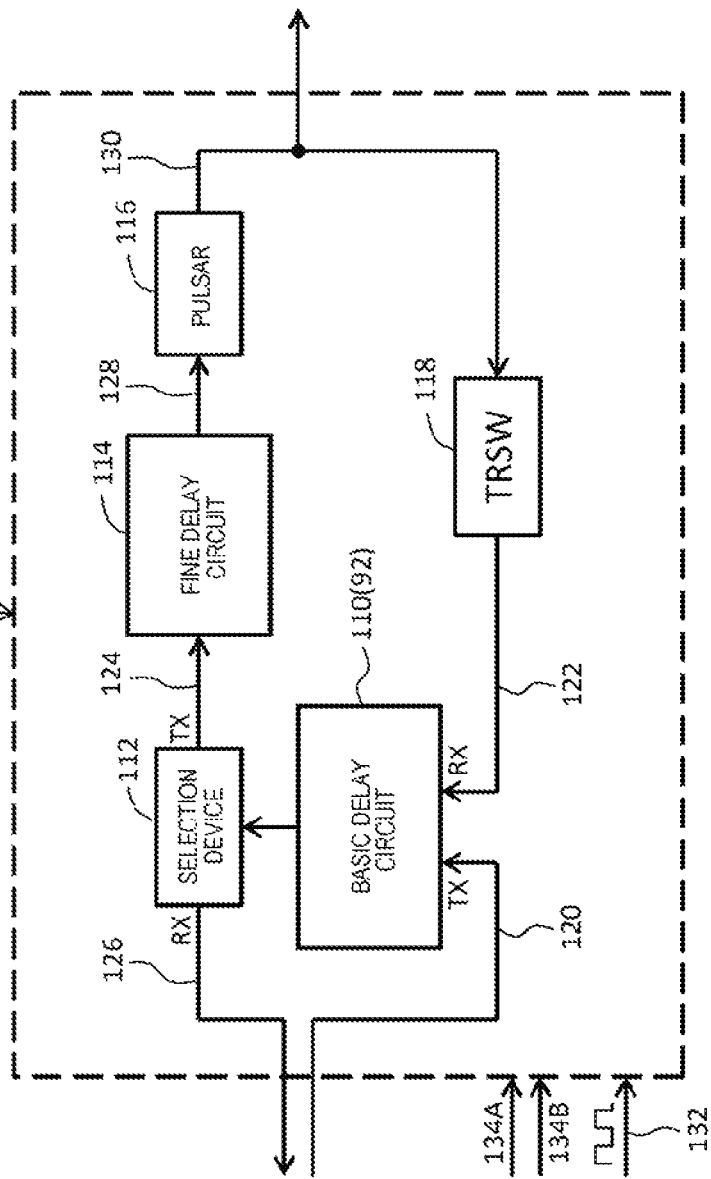
FIG. 6 is a block diagram illustrating a basic configuration of a transmission and reception circuit.

In FIG. 6, a basic configuration of the transmission and reception circuit 32 is illustrated as a block diagram. A basic delay circuit 110 is equivalent to the delay circuit 92 illustrated in FIG. 3, and is a delay circuit that functions at the time of transmission and reception. In the embodiment, the basic delay circuit 110 is constituted by an analog random access memory (ARAM). The basic delay circuit operates in accordance with a basic clock 132. For example, the basic delay circuit 110 includes a plurality of delay cells (capacitors) and switching circuits. The number of delay cells capable of realizing a required maximum delay amount is provided. At the time of transmission, a transmission signal 120 is delayed by the basic delay circuit 110, and the transmission signal delayed is output to a TX side of the selection device 112 (see reference numeral 124). The transmission signal 120 is a signal generated in the transmission main beamformer. At the time of reception, the reception signal 122 is delayed by the basic delay circuit 110, and the reception signal 126 delayed is output to an RX side of the selection device 112. The reception signal 126 is output to the reception main beamformer. In this manner, the basic delay circuit 110 functions at the time of transmission and reception.

A fine delay circuit 114 functions at the time of transmission and has a delay device column and a selector as will be described later in detail. The delay device column operates at a high speed in accordance with a pair of clocks illustrated in FIG. 7 later. The fine delay circuit 114 compensates for a quantized delay error. Accordingly, it is possible to improve the form of a transmission beam. A pulsar 116 is a circuit that generates a transmission pulse 130 as a transmission driving signal using an input transmission signal 128 as a trigger. The transmission pulse 130 is output to a vibration element. A linear amplifier may be provided instead of the pulsar 116.

The reception signal 122 from the vibration element is input to the basic delay circuit 110 through a transmission and reception changeover switch (TRSW) 118. The basic clock 132, a row control signal 134A, and a column control signal 134B are given to the transmission and reception circuit 32. A signal for specifying a basic delay time (average delay time) and a signal for compensating for a quantized delay error are respectively included in the row control signal 134A and the column control signal 134B.

Figure 7:
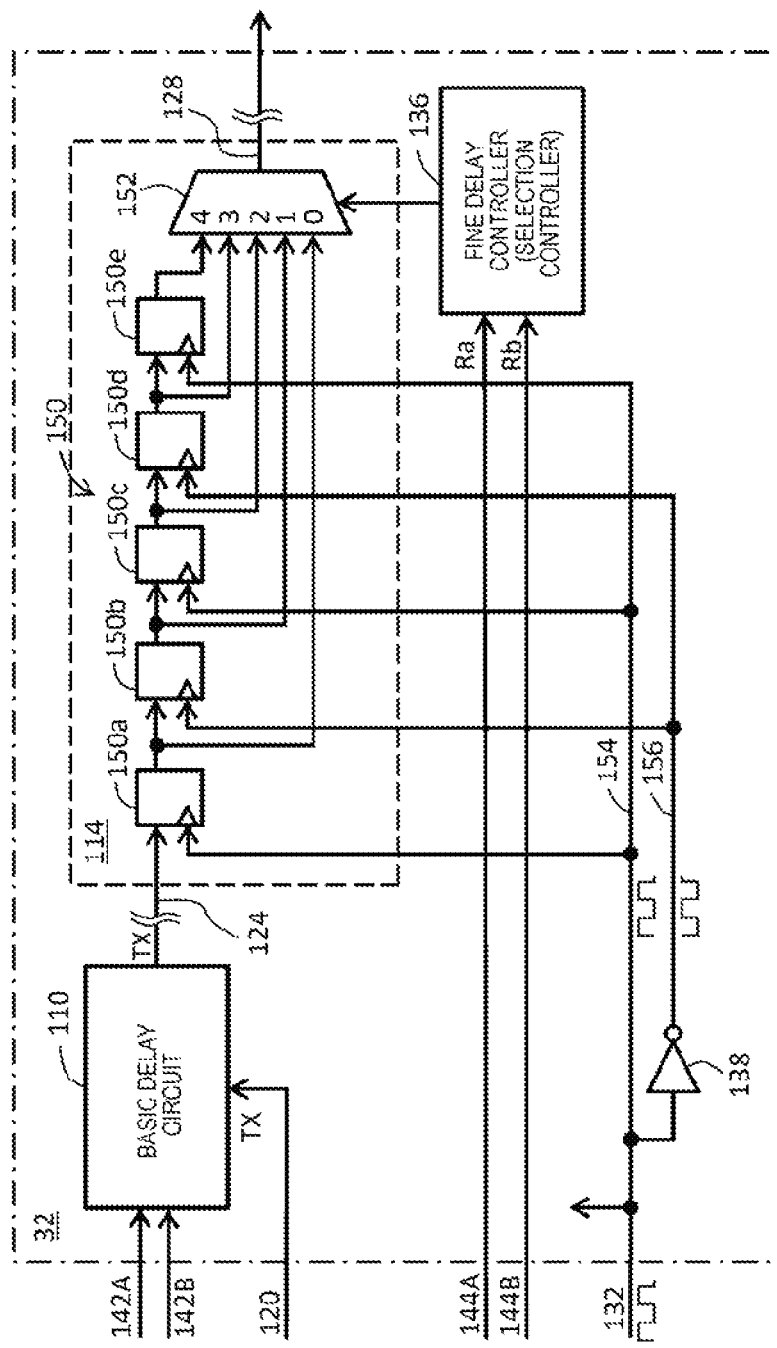
FIG. 7 is a circuit diagram illustrating a first example of a transmission and reception circuit.

In FIG. 7, a configuration related to transmission in the transmission and reception circuit 32 is specifically illustrated. The transmission and reception circuit 32 illustrated in the drawing is a transmission and reception circuit according to a first example.

A row control signal 142A indicating an average delay time in units of a row is input to the basic delay circuit 110, and a column control signal 142B indicating an average delay time in units of a column is input to the basic delay circuit 110. The basic delay circuit 110 executes delay on the basis of two average delay times. In this case, a basic delay time may be calculated by adding up the two average delay times, an input signal may be delayed on the basis of the calculated basic delay time, the two average delay times may be used as independent parameters, and an input signal may be delayed in accordance with the average delay times. Other methods may be adopted. In either case, the transmission signal 120 is delayed in the basic delay circuit 110. The delayed transmission signal 124 is input to the fine delay circuit 114.

The fine delay circuit 114 is constituted by a delay device column 150 and a selector 152. The delay device column 150 is constituted by a plurality of delay devices 150*a* to 150*e* connected to each other in series. Each of the delay devices 150*a* to 150*e* is constituted by a delay cell, a register, a sample and hold circuit, and the like, and is a circuit that holds and outputs an input analog voltage value. An analog shift register is configured as the entire delay device column 150. Each of the delay devices 150*a* to 150*e* operates in synchronization with a pair of clocks 154 and 156.

In the configuration example illustrated in the drawing, a phase inverting circuit 138 is provided within the transmission and reception circuit 32. The phase inverting circuit 138 is used to constitute the pair of clocks 154 and 156 having phases different from each other by 180 degrees on the basis of the basic clock 132 supplied from a control circuit. Although the frequency of each of the clocks 154 and 156 is the same as the frequency of the basic clock 132, the phases of the clocks are shifted by 180 degrees, and such a pair of clocks 154 and 156 are alternately supplied to the plurality of delay devices 150*a* to 150*e*. Accordingly, a unit delay time of the fine delay circuit 114 is half of the unit delay time of the basic delay circuit 110. This means that the accuracy of delay of the fine delay circuit 114 is twice the accuracy of delay of the basic delay circuit 110 and means that the delay device column 150 operates at a speed twice as fast as that of the basic delay circuit 110 as a whole. In the delay devices 150*a* to 150*e*, the sampling and holding of an input signal are performed in synchronization with the input clock 154 or 156. The pair of clocks 154 and 156 may be generated outside. Alternatively, a multiplication circuit may be provided within the transmission and reception circuit 32, a clock having a frequency twice as high as the frequency of the basic clock may be generated, and the delay device column 150 may be operated using the clock. Alternatively, the delay device column 150 may be operated using a pair of clocks having a frequency twice as high as the frequency of the basic clock and having phases different from each other by 180 degrees. In this case, the delay device column 150 operates at a quadruple speed as a whole. Alternatively, each of the delay devices 150*a* to 150*e* may be configured to operate at a speed twice as fast as the basic clock 132. An operation speed of the delay device column 150 may be set to be equal to or more than three times the operation speed of the basic delay circuit 110. The configuration and operation of the delay device column 150 may be changed in accordance with a mode of a clock to be supplied to the delay device column 150.

Among the delay devices 150*a* to 150*e*, the delay device 150*a* at the front functions as a buffer for aligning a timing, and the remaining four delay devices 150*b* to 150*e* take charge in fine delay. Five signals are extracted as candidate signals from five extraction points in the delay device column 150, and these signals are given to input terminals 0 to 4 of the selector 152. The selector 152 is a circuit that selects a specific signal from among the signals.

A fine delay controller 136 functions as a selection controller, and is a circuit that controls the operation of the selector 152 in accordance with two control values indicated by two control signals 144A and 144B. The two control signals 144A and 144B are equivalent to a row control signal and a column control signal, and specifically, these signals have a row control value Ra and a column control value Rb. A candidate signal to be selected is specified by a combination of the signals. Actually, the fine delay controller 136 sets the operation of the selector 152 before transmission is started.

Figure 8:
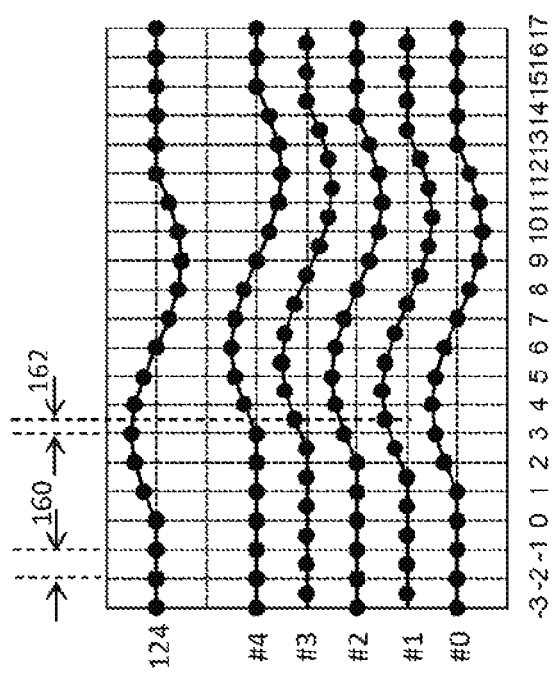
FIG. 8 is a timing chart illustrating an operation of a fine delay circuit.

In FIG. 8, the operation of a delay device column is illustrated. The horizontal axis represents a time axis. Reference numeral 124 denotes a transmission signal before fine delay, that is, an input signal. In the example illustrated in the drawing, the input signal is a sinusoidal wave, but the input signal may be a pulsed signal. In a case where a sinusoidal wave is desired to be supplied to a vibration element, it is desirable to provide a linear amplifier instead of the pulsar illustrated in FIG. 6.

In addition, #0 to #4 indicate a plurality of candidate signals delayed in a stepwise manner. For example, #0 is a candidate signal output from a delay device at the front, and is a signal equivalent to a fine delay amount of 0. In addition, #4 is a candidate signal output from the last delay device. Reference numeral 160 denotes a unit delay amount in the basic delay circuit. Reference numeral 162 denotes a unit delay amount in the fine delay circuit. For example, in a case where the frequency of the basic clock is 40 MHz, the unit delay amount 160 is 25 ns, and the unit delay amount 162 is 12.5 ns. In a case where the frequency of the basic clock is 50 MHz, the unit delay amount 160 is 20 ms, and the unit delay amount 162 is 10 ns. A fine delay amount is selected for each vibration element so that a quantized delay error is compensated for.

Operation conditions in the first example will be described using FIG. 9. A table 164 shows a relationship between a quantized delay error 168 in units of a row/in units of a column, a compensation delay time 170, and a row control code/column control code (Ra/Rb) 172. A quantized delay error between −0.5 and +0.5 may occur in units of a row or in units of a column. Here, 1.0 is equivalent to a unit delay amount in the basic delay circuit. Since the fine delay circuit cannot handle a negative time, a compensation delay time is obtained in consideration of the negative time.

A control code specifies each compensation delay time. A row control code (row control value) is indicated by Ra, and a column control code (column control value) is indicated by Rb. The former code is a code for compensating for a quantized delay error occurring for each row, and the latter code is a code for compensating for a quantized delay error occurring for each column. A table 166 shows a relationship between two control codes Ra and Rb and candidate signal numbers. A numerical value written in each cell 174 indicates a candidate signal number. For example, an input terminal of #0 in the selector is selected in a case where 0 is specified, and an input terminal of #4 in the selector is selected in a case where 4 is specified. For example, the control codes Ra and Rb are generated in the control circuit within the electronic circuit on the basis of the transmission and reception control unit within the device main body.

In this manner, in the embodiment, a quantized delay error in units of a row and a quantized delay error in units of a column are treated differently, and a fine delay time is determined in accordance with a combination of two control signals in order to collectively compensate for the quantized delay errors.

Figure 10:
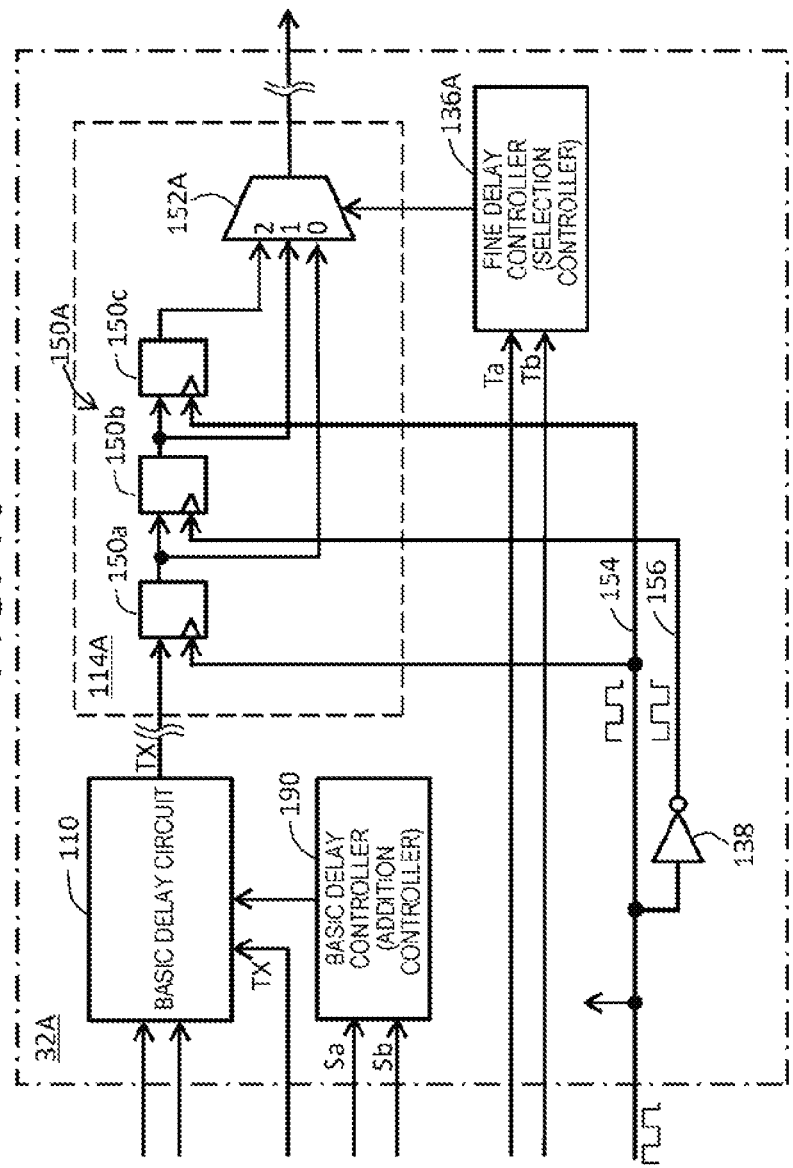
FIG. 10 is a circuit diagram illustrating a second example of a transmission and reception circuit.

In FIG. 10, a transmission and reception circuit 32A according to a second example is illustrated. The same components as those illustrated in FIG. 7 are denoted by the same reference numerals, and the description thereof will be omitted.

In the second example, a quantized delay error is compensated for by using both a basic delay circuit 110 and a fine delay circuit 114A. Specifically, a row control value Sa indicating (the entirety or a portion of) an integer portion in a compensation delay amount in units of a row and a column control value Sb indicating (the entirety or a portion of) an integer portion in a compensation delay amount in units of a column are given to a basic delay controller 190. The basic delay controller 190 executes control of adding a delay time for one unit to a basic delay time in a case where the row control value Sa is 1 and similarly adding a delay time for one unit to a basic delay time in a case where the column control value Sb is 1. That is, the basic delay controller executes control of performing addition and correction of a basic delay time.

According to such addition and correction, it is possible to reduce the scale of a delay device column 150A included in the fine delay circuit 114A. In the second example, the delay device column 150A is constituted by three delay devices 150a to 150c. Three candidate signals extracted from the delay device column 150A are given to three input terminals in a selector 152A. The delay device column 150A operates at a high speed in accordance with a pair of clocks.

A fine delay controller 136A controls the operation of the selector 152A on the basis of a row control value Ta and a column control value Tb which are input. The row control value Ta indicates a decimal portion in a compensation delay amount in units of a row, and the column control value Tb indicates a decimal portion in a compensation delay amount in units of a column. A portion of an integer portion may be compensated for in fine delay.

Figure 11:
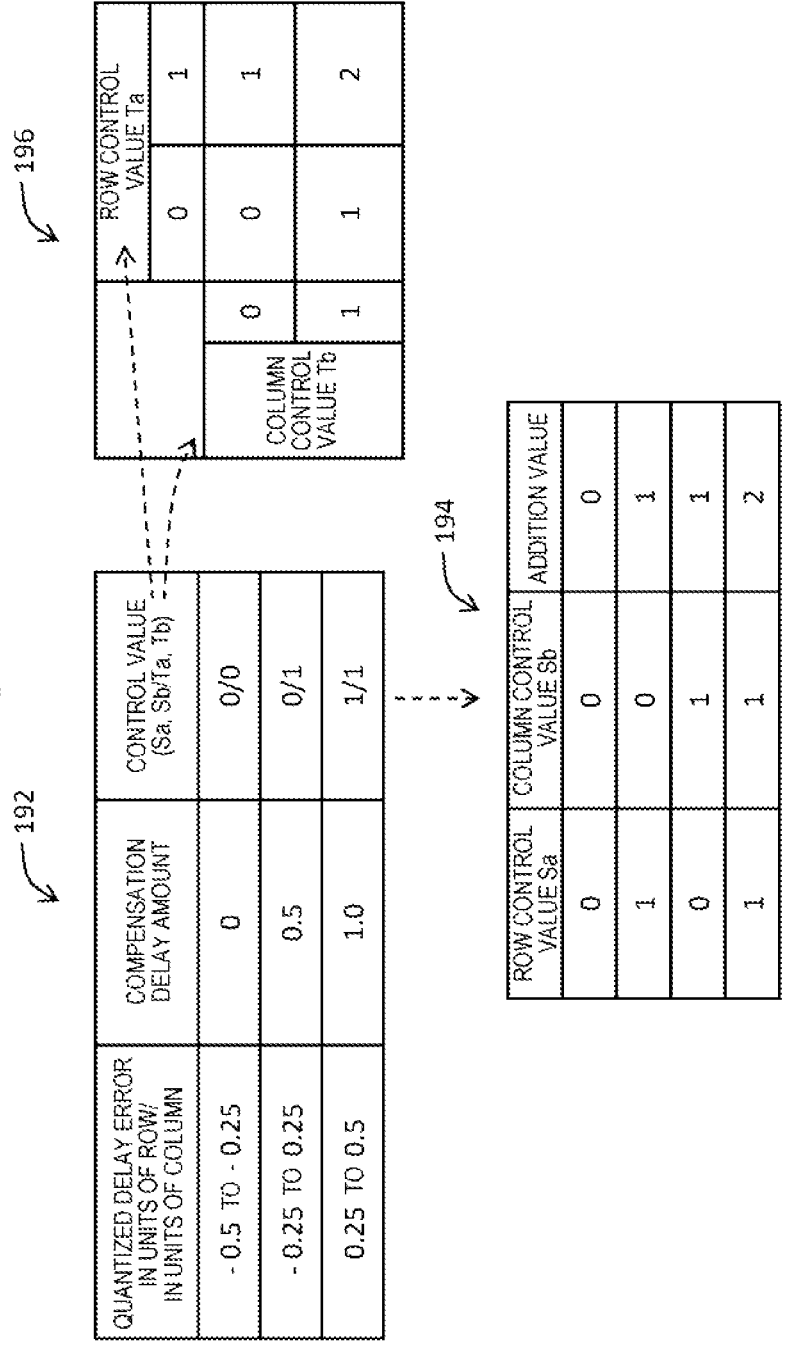
FIG. 11 is a diagram illustrating compensation control according to the second example.

Operation conditions in the second example will be described using FIG. 11. A table 192 shows a relationship between a quantized delay error in units of a row/in units of a column, a compensation delay time, and a control value (Sa, Sb/Ta, Tb) in units of a row/in units of a column. A basic delay controller illustrated in FIG. 10 operates in accordance with contents of a table 194. That is, an addition value is determined in accordance with a combination of the row control value Sa and the column control value Sb, and a unit delay amount equivalent to the addition value is added to a basic delay time. However, as a result, necessary compensation may be performed for the basic delay time, and for example, compensation based on the row control value Sa and compensation based on the column control value Sb may be independently executed. The fine delay controller 136A illustrated in FIG. 10 operates in accordance with contents of a table 196. That is, a candidate signal to be selected in the selector is determined by a combination of the row control value Ta and the column control value Tb.

In this manner, according to the second example, the compensation of a quantized delay error can be performed using both a basic delay circuit and a fine delay circuit, and thus it is possible to obtain an advantage that a circuit scale can be reduced as compared to the first embodiment.

Figure 12:
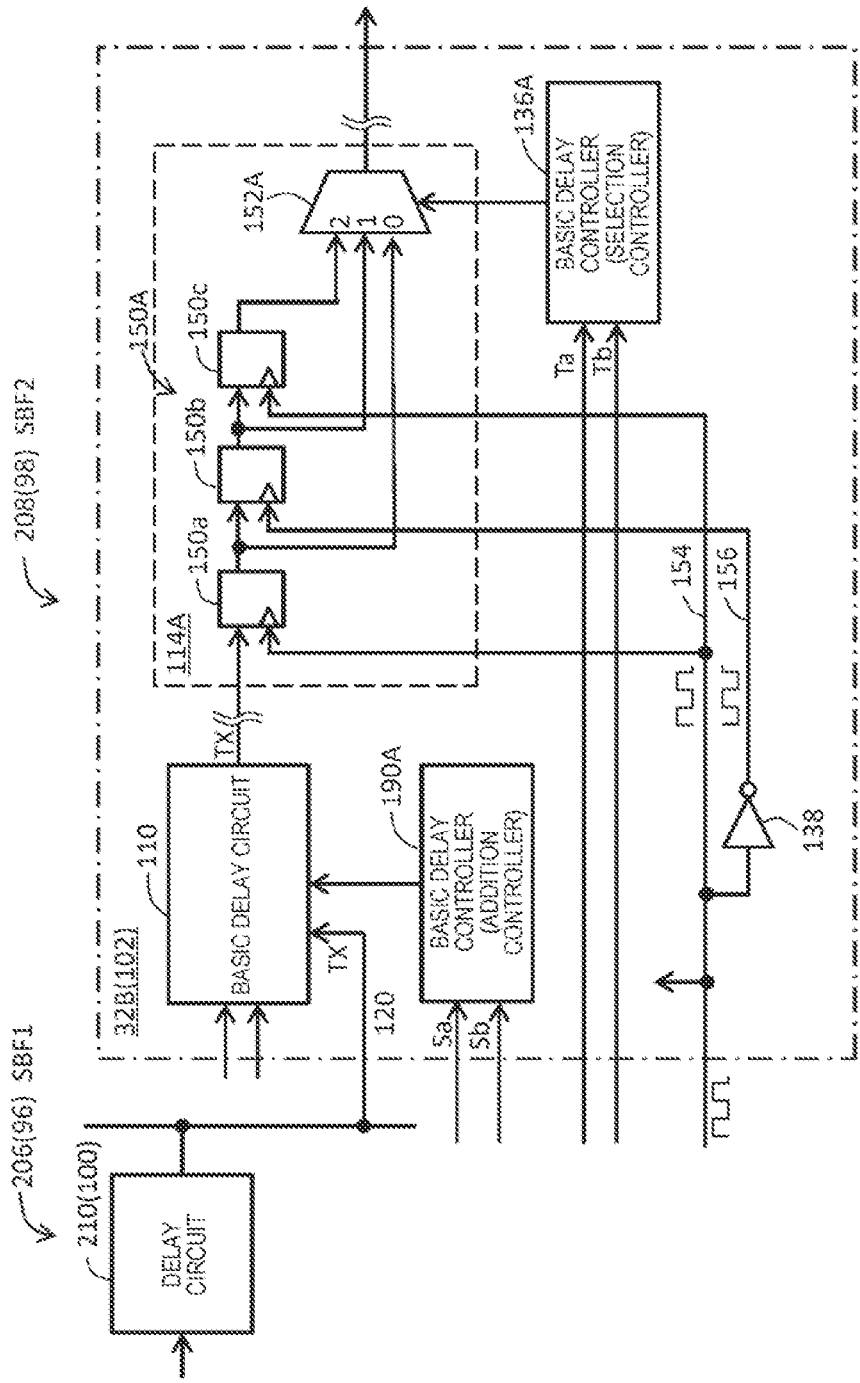
FIG. 12 is a circuit diagram illustrating a third example of a transmission and reception circuit.

In FIG. 12, a transmission and reception circuit 32B according to a third example is illustrated. The same components as those illustrated in FIGS. 7 and 10 are denoted by the same reference numerals, and the description thereof will be omitted.

The transmission and reception circuit 32B basically has the same configuration as that of the transmission and reception circuit 32A illustrated in FIG. 10. However, operation conditions in this example are partially different from the operation conditions in the second example as described in FIG. 13 later.

The third example assumes the two-stage sub beamforming illustrated in FIG. 4. SBF1 of a first stage is denoted by reference numeral 206. The SBF1 is equivalent to SBF1 (96) illustrated in FIG. 4. SBF2 of a second stage is denoted by reference numeral 208. The SBF2 is equivalent to SBF2 (98) illustrated in FIG. 4. In FIG. 12, a delay circuit 210 included in SBF1 (206) is illustrated. The delay circuit 210 is equivalent to the delay circuit 100 illustrated in FIG. 4. The transmission and reception circuit 32B is equivalent to the delay circuit 102 illustrated in FIG. 4.

Figure 13:
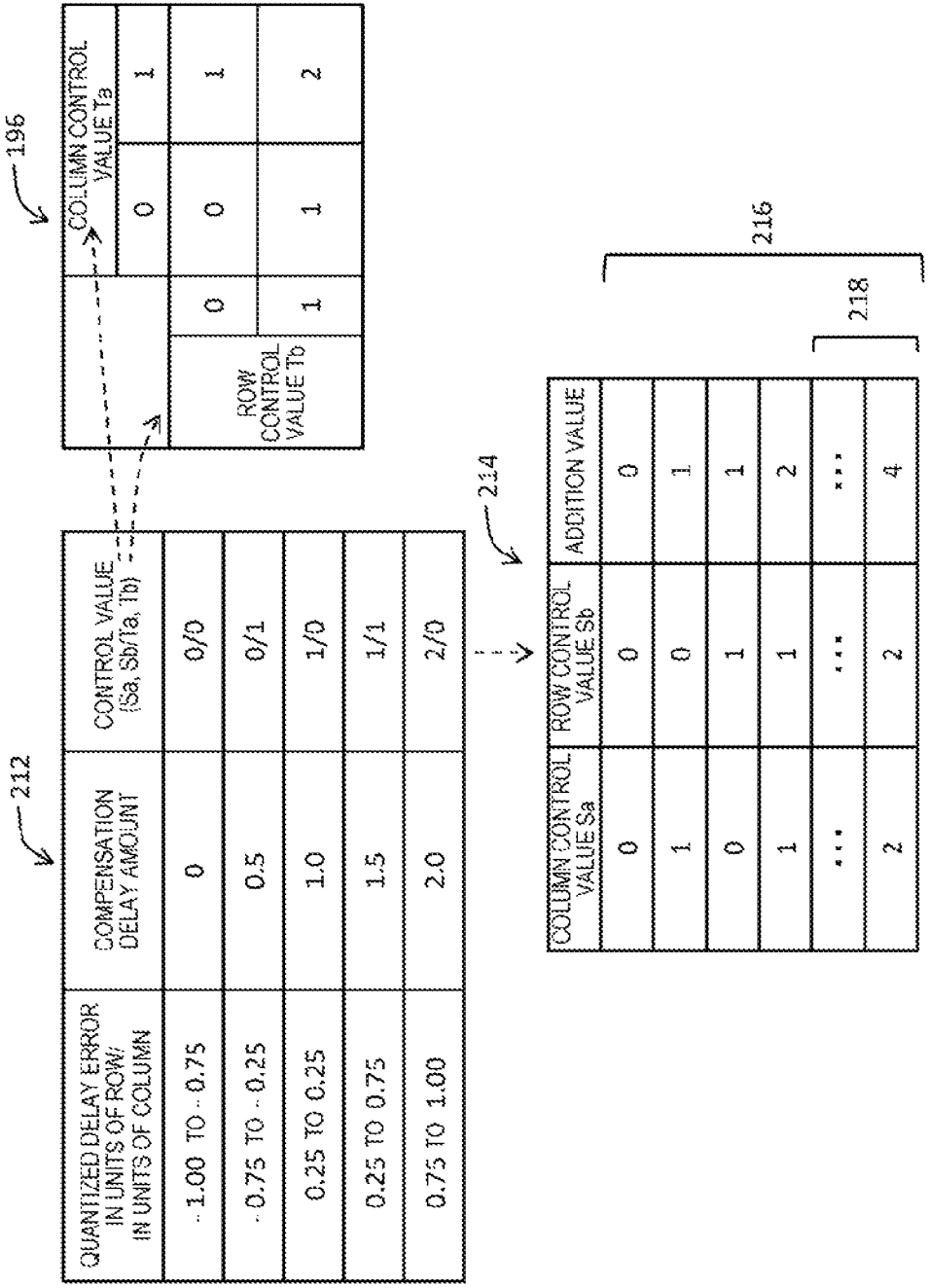
FIG. 13 is a diagram illustrating compensation control according to a third example.

In FIG. 13, operation conditions in the third example are illustrated. A table 212 shows a relationship between a quantized delay error in units of a row/in units of a column, a compensation delay time, and a control value (Sa, Sb/Ta, Tb) in units of a row/in units of a column. Since matrix control is applied in the sub beamforming of each stage, a quantized delay error between −1.00 and +1.00 may occur for each row and each column in the two-stage sub beamforming as a whole. In order to compensate for such a quantized delay error, the control values Sa and Sb change between 0 and 2. The control values Ta and Tb have a value of 0 or 1, similar to the second example.

The basic delay controller operates in accordance with contents of a table 214. That is, an addition value is determined in accordance with a combination of the row control value Sa and the column control value Sb, and a delay amount equivalent to the addition value is added to a basic delay time. In a case where the addition value is 4, four times a unit delay amount is added. However, as described above, as a result, necessary compensation may be performed for the basic delay time, and for example, compensation based on the row control value Sa and compensation based on the column control value Sb may be independently executed. As denoted by reference numeral 216, control may be performed over the entire range (the entire range of a compensation delay amount) of the addition value, but a delay compensation amount may be suppressed to 1.5 in a case where the delay compensation amount is likely to be 2. This means that an upper limit of a delay compensation amount is set to 1.5 (in this case, an upper limit of an addition value is set to 2). A partial range to which such an upper limit is applied is denoted by reference numeral 218. For example, in a case where the partial range 218 is rarely applicable, it is particularly desirable to adopt such a modification example. According to the modification example, each of the row control value Sa and the column control value Sb can be expressed by one bit, and control information can be reduced. The fine delay controller operates in accordance with contents of a table 196 illustrated in FIG. 13. The contents of the table 196 are the same as those of the table 196 illustrated in FIG. 10.

In this manner, according to the third example, in a case where transmission sub beamforming is executed in a stepwise manner, it is possible to collectively compensate for a quantized delay error occurring in transmission sub beamforming over a plurality of stages and a quantized delay error occurring due to delay control in units of a row and a column.

Figure 14:
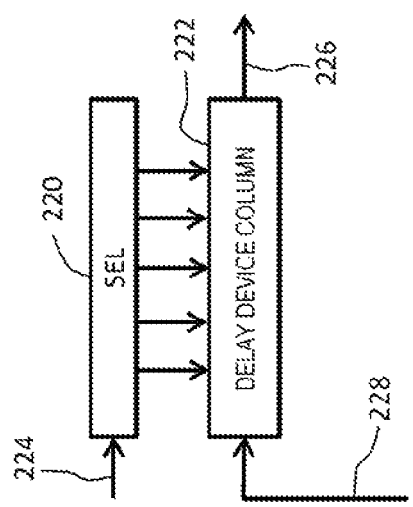
FIG. 14 is a diagram illustrating another configuration example of a fine delay circuit.

In FIG. 14, a modification example of the fine delay circuit is illustrated. The fine delay circuit is constituted by a selector 220 and a delay device column 222. The delay device column 222 is constituted by a plurality of delay devices connected to each other in series. These delay devices operate in synchronization with a high-speed clock 228. The selector 220 selects a fine delay time by selecting an input terminal included in the delay device column 222. The selector 220 operates before transmission is started. A transmission signal 224 is input to the delay device column 222 operating at a high speed through the input terminal selected by the selector 220. The delay device column 222 functions as a shift register, and a delayed transmission signal 226 having been subjected to fine delay is output from the output thereof.

Figure 15:
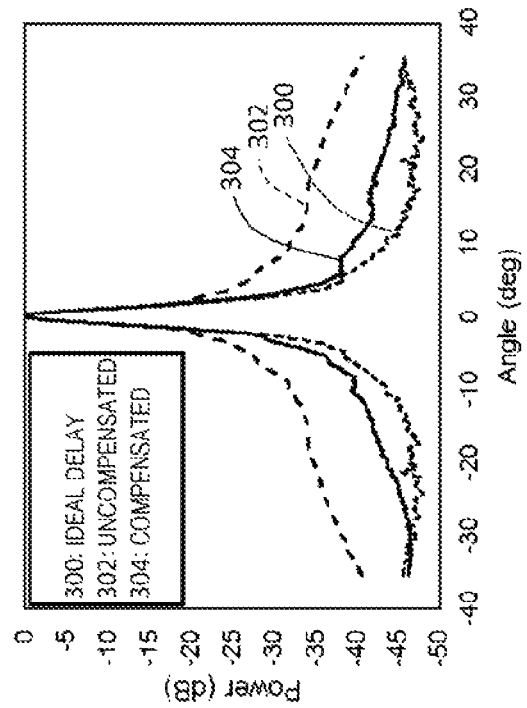
FIG. 15 is a diagram illustrating effects of delay error compensation.

In FIG. 15, effects of the embodiment are illustrated. The horizontal axis represents the θ-direction illustrated in FIG. 2. The vertical axis represents a transmission power. Reference numeral 300 denotes an ideal profile in a case where there is no quantized delay error. Reference numeral 302 denotes a profile in a case where compensation for a quantized delay error is not performed. Reference numeral 304 denotes a profile in a case where compensation for a quantized delay error is performed. In a case where compensation for a quantized delay error is not performed, a side lobe becomes considerably large. On the other hand, in a case where compensation for a quantized delay error is performed, that is, according to the embodiment, the beam profile 304 becomes close to the beam profile 300, and it is possible to effectively suppress a side lobe. According to the embodiment, a strain of a transmission beam can be improved, and thus it is possible to enhance image quality particularly in a case where harmonic imaging is performed.

As described above, according to the embodiment, it is possible to achieve both the suppression of an increase in a circuit scale and an improvement in the accuracy of transmission delay. In addition, it is possible to form a satisfactory transmission beam by compensating for a delay error for each vibration element.

In the above-described embodiment, a row control signal and a column control signal for delay error compensation are given to each transmission and reception circuit, but a control signal obtained by integrating the signals may be given. A combination of the basic delay circuit and the fine delay circuit disclosed in the embodiment may also be provided in a transmission beamformer to which control other than matrix control is applied. Although a quantized delay error is exclusively compensated for in the above-described embodiment, other delay errors may be compensated for in the fine delay circuit.

What is claimed is:

1. An ultrasonic diagnostic device comprising:
    a vibration element array which is provided within an ultrasonic probe and is constituted by a plurality of vibration elements arrayed two-dimensionally;
    an element circuit array which is provided within the ultrasonic probe, is constituted by a plurality of element circuits connected to the plurality of vibration elements, and has a sub beamforming function; and
    a control circuit that applies matrix control, which is a combination of row unit delay control and column unit delay control, to the element circuit array, wherein
    each of the plurality of element circuits includes:
        a basic delay circuit which delays a transmission signal; and
        a fine delay circuit which is configured to be capable of performing delay finer than that of the basic delay circuit and delays an output of the transmission signal from the basic delay circuit;
    the basic delay circuit operates in accordance with a basic clock; and
    the fine delay circuit operates in accordance with a plurality of clocks having different phases and generated from the basic clock, wherein
    a row control signal for compensating for a first quantized delay error occurring through the row unit delay control and a column control signal for compensating for a second quantized delay error occurring through the column unit delay control are given to each of the plurality of element circuits, and the fine delay circuit delays the transmission signal in accordance with the row control signal and the column control signal, to thereby compensate for the first quantized delay error and the second quantized delay error.

2. The ultrasonic diagnostic device according to claim 1, wherein the fine delay circuit includes:

a delay device column to which the output from the basic delay circuit is input and which is constituted by a plurality of delay devices connected to each other in series; and a selection device which selects any one candidate signal, from among a plurality of candidate signals output from the delay device column and delayed in a stepwise manner, as the transmission signal subjected to fine delay in accordance with the row control signal and the column control signal.

3. The ultrasonic diagnostic device according to claim 1, wherein the row control signal includes a first row control signal for compensating for a third quantized delay error occurring through the row unit delay control and a second row control signal for compensating for the first quantized delay error occurring through the row unit delay control the column control signal includes a first column control signal for compensating for a fourth quantized delay error occurring through the column unit delay control and a second column control signal for compensating for the second quantized delay error occurring through the column unit delay control, a basic delay controller which corrects a first delay amount of the basic delay circuit in accordance with the first row control signal and the first column control signal is provided, and a fine delay controller which selects a second delay amount of the fine delay circuit in accordance with the second row control signal and the second column control signal is provided.

4. The ultrasonic diagnostic device according to claim 1, further comprising:

a transmission main beamformer; and a transmission sub beamformer group which is provided between the transmission main beamformer and the vibration element array, wherein the element circuit array constitutes the transmission sub beamformer group.

5. The ultrasonic diagnostic device according to claim 1, further comprising:

a transmission main beamformer; and a plurality of transmission sub beamformers groups which are provided in a stepwise manner between the transmission main beamformer and the vibration element array, wherein the element circuit array constitutes a first transmission sub beamformer group, among the plurality of transmission sub beamformers groups, that is closest to the vibration element array.

6. The ultrasonic diagnostic device according to claim 1, wherein the basic delay circuit is for transmission and reception, and the fine delay circuit is for the transmission.

7. An ultrasonic probe comprising:

a vibration element array which is constituted by a plurality of vibration elements;

an element circuit array which is constituted by a plurality of element circuits connected to the plurality of vibration elements; and a control circuit that applies matrix control, which is a combination of row unit delay control and column unit delay control, to the element circuit array, wherein each of the plurality of element circuits includes a basic delay circuit which delays a transmission signal, and a fine delay circuit which is configured to be capable of performing delay finer than that of the basic delay circuit and delays an output of the transmission signal from the basic delay circuit;

the basic delay circuit operates in accordance with a basic clock; and the fine delay circuit operates in accordance with a plurality of clocks having different phases and generated from the basic clock, wherein a row control signal for compensating for a first quantized delay error occurring through the row unit delay control and a column control signal for compensating for a second quantized delay error occurring through the column unit delay control are given to each of the plurality of element circuits, and the fine delay circuit delays the transmission signal in accordance with the row control signal and the column control signal, to thereby compensate for the first quantized delay error and the second quantized delay error.

* * * * *